United States Patent
Iimura et al.

(10) Patent No.: US 9,944,772 B2
(45) Date of Patent: Apr. 17, 2018

(54) ORGANOSILOXANE, CURABLE SILICONE COMPOSITION, AND SEMICONDUCTOR DEVICE

(71) Applicant: Dow Corning Toray Co., Ltd., Tokyo (JP)

(72) Inventors: Tomohiro Iimura, Ichihara (JP); Nohno Toda, Ichihara (JP); Sawako Inagaki, Ichihara (JP); Yusuke Miyamoto, Ichihara (JP); Haruhiko Furukawa, Ichihara (JP)

(73) Assignee: DOW CORNING TORAY CO., LTD., Chiyoda-ku, Tokyo (JP)

( * ) Notice: Subject to any disclaimer, the term of this patent is extended or adjusted under 35 U.S.C. 154(b) by 10 days.

(21) Appl. No.: 15/315,750

(22) PCT Filed: May 29, 2015

(86) PCT No.: PCT/JP2015/002718
§ 371 (c)(1),
(2) Date: Feb. 17, 2017

(87) PCT Pub. No.: WO2015/186324
PCT Pub. Date: Dec. 10, 2015

(65) Prior Publication Data
US 2017/0204252 A1    Jul. 20, 2017

(30) Foreign Application Priority Data
Jun. 4, 2014    (JP) .................................. 2014-115579

(51) Int. Cl.
*H01L 23/29*    (2006.01)
*C08K 5/544*    (2006.01)
(Continued)

(52) U.S. Cl.
CPC .......... *C08K 5/5442* (2013.01); *C07D 405/14* (2013.01); *C08G 77/388* (2013.01);
(Continued)

(58) Field of Classification Search
CPC ............... C08L 2203/206; H01L 33/56; H01L 2924/181; H01L 33/52; H01L 23/293;
(Continued)

(56) References Cited

U.S. PATENT DOCUMENTS

| 4,374,986 A | 2/1983 | Renner et al. |
| 4,406,807 A | 9/1983 | Renner et al. |

(Continued)

FOREIGN PATENT DOCUMENTS

| CN | 101538367 A | 9/2009 |
| CN | 101735617 A | 6/2010 |

(Continued)

OTHER PUBLICATIONS

International Search Report for Application No. PCT/JP2015/002718 dated Aug. 18, 2015, 6 pages.
(Continued)

*Primary Examiner* — Roy Potter
(74) *Attorney, Agent, or Firm* — Howard & Howard Attorneys PLLC

(57) ABSTRACT

An organosiloxane represented by the following general formula; a curable silicone composition comprising: (A) an organopolysiloxane having at least two alkenyl groups in a molecule; (B) an organohydrogenpolysiloxane having at least two silicon atom-bonded hydrogen atoms in a molecule; (C) an adhesion promoter containing the organosiloxane; and (D) a catalyst for hydrosilylation reaction; and a semiconductor device in which a semiconductor element is encapsulated with a cured product of the composition. A novel organosiloxane, a curable silicone composition that
(Continued)

contains the novel organosiloxane as an adhesion promoter and that forms a cured product having excellent adhesion to various base materials, and a semiconductor device that is formed by using the composition and that has excellent reliability are provided.

10 Claims, 1 Drawing Sheet

(51) Int. Cl.

| | | |
|---|---|---|
| C07D 405/14 | (2006.01) | |
| C08G 77/388 | (2006.01) | |
| C08L 83/08 | (2006.01) | |
| H01L 33/56 | (2010.01) | |

(52) U.S. Cl.
CPC ............ C08L 83/08 (2013.01); H01L 23/296 (2013.01); H01L 33/56 (2013.01); *C08L 2203/206* (2013.01); *C08L 2205/025* (2013.01)

(58) Field of Classification Search
CPC .. H01L 23/296; H01L 31/048; H01L 31/0481
See application file for complete search history.

(56) References Cited

U.S. PATENT DOCUMENTS

| | | | | |
|---|---|---|---|---|
| 5,399,650 | A | * | 3/1995 | Bilgrien .................. C08G 77/18 528/15 |
| 5,399,651 | A | * | 3/1995 | Gentle ..................... C08G 77/20 528/15 |
| 7,985,806 | B2 | | 7/2011 | Shiobara et al. |
| 8,088,856 | B2 | | 1/2012 | Shiobara et al. |
| 2009/0203822 | A1 | | 8/2009 | Shiobara et al. |
| 2010/0125116 | A1 | | 5/2010 | Shiobara et al. |
| 2011/0254047 | A1 | * | 10/2011 | Yoshitake ............... C08L 83/04 257/100 |
| 2016/0208055 | A1 | * | 7/2016 | Horstman ............ C09D 183/10 |

FOREIGN PATENT DOCUMENTS

| | | |
|---|---|---|
| EP | 2 083 038 A1 | 7/2009 |
| EP | 2 186 844 A1 | 5/2010 |
| JP | 2000-344895 A | 12/2000 |
| JP | 2009-275206 A | 11/2009 |
| JP | 2010-065161 A | 3/2010 |
| JP | 2010-138380 A | 6/2010 |
| JP | 2011-057755 A | 3/2011 |
| JP | 2011-208120 A | 10/2011 |
| JP | 2012-052029 A | 3/2012 |
| KR | 10-2009-0082868 A | 7/2009 |
| KR | 10-2010-0054740 A | 5/2010 |
| TW | 200932794 A2 | 8/2009 |
| TW | 201035154 A | 10/2010 |

OTHER PUBLICATIONS

English language abstract for CN 101538367 extracted from espacenet.com database on Feb. 1, 2017, 1 page.
English language abstract for CN 101735617 extracted from espacenet.com database on Feb. 1, 2017, 1 page.
English language abstract and machine-assisted English translation for JP 2000-344895 extracted from espacenet.com database on Feb. 1, 2017, 12 pages.
English language abstract for JP 2009-275206 extracted from espacenet.com database on Feb. 1, 2017, 2 pages.
English language abstract and machine-assisted English translation for JP 2010-065161 extracted from espacenet.com database on Feb. 1, 2017, 21 pages.
English language abstract for JP 2010-138380 extracted from espacenet.com database on Feb. 1, 2017, 1 page.
English language abstract and machine-assisted English translation for JP 2011-057755 extracted from espacenet.com database on Feb. 1, 2017, 18 pages.
English language abstract and machine-assisted English translation for JP 2011-208120 extracted from espacenet.com database on Feb. 1, 2017, 25 pages.
English language abstract and machine-assisted English translation for JP 2012-052029 extracted from espacenet.com database on Feb. 1, 2017, 22 pages.
English language abstract for KR 10-2009-0082868 extracted from espacenet.com database on Feb. 1, 2017, 2 pages.
English language abstract for KR 10-2010-0054740 extracted from espacenet.com database on Feb. 1, 2017, 1 page.
English language abstract for TW 200932794 extracted from espacenet.com database on Feb. 1, 2017, 2 pages.
English language abstract for TW 201035154 extracted from espacenet.com database on Feb. 1, 2017, 1 page.

* cited by examiner

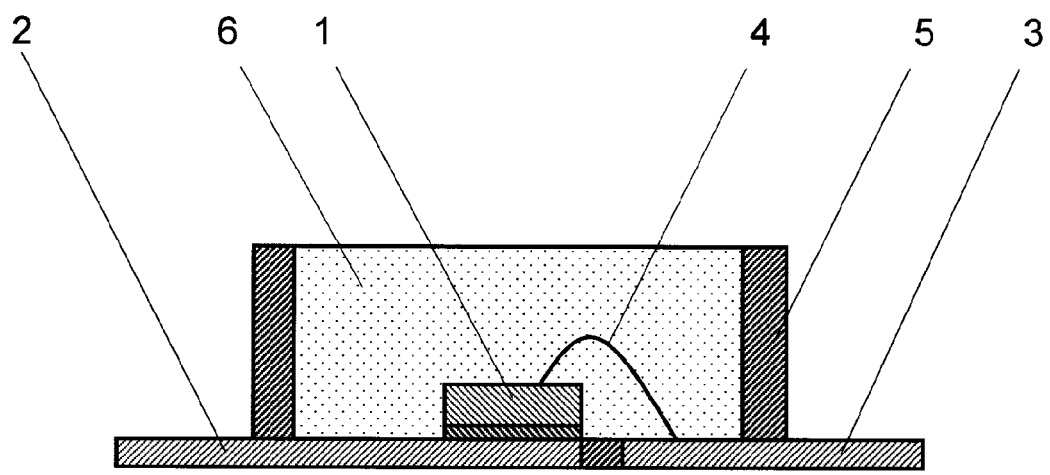

ORGANOSILOXANE, CURABLE SILICONE COMPOSITION, AND SEMICONDUCTOR DEVICE

CROSS-REFERENCE TO RELATED APPLICATIONS

This application is the National Stage of International Patent Application No. PCT/JP2015/002718, filed on May 29, 2015, which claims priority to and all the advantages of Japanese Patent Application No. 2014-115579, filed on Jun. 4, 2014, the content of which is incorporated herein by reference.

TECHNICAL FIELD

The present invention relates to a novel organosiloxane, a curable silicone composition containing the organosiloxane as an adhesion promoter, and a semiconductor device produced by using such a composition.

BACKGROUND ART

Since a hydrosilylation curable silicone composition typically has poor adhesion to metals and organic resins, especially to base materials of thermoplastic resins or the like, the following proposals have been made, for example. A curable silicone composition comprising: an organopolysiloxane having an alkenyl group bonded to a silicon atom; an organohydrogenpolysiloxane having a silicon atom-bonded hydrogen atom; an adhesion promoter containing an isocyanuric acid derivative having at least one type of functional group selected from the group consisting of epoxy groups, glycidoxy groups, and alkoxysilyl groups, and at least one type of group selected from the group consisting of cross-linkable vinyl groups and hydrosilyl groups (Si—H groups); and a catalyst for hydrosilylation reaction has been proposed (see Patent Document 1). A curable silicone composition comprising: an organopolysiloxane having at least two alkenyl groups in a molecule; an organohydrogenpolysiloxane having at least two silicon atom-bonded hydrogen atoms in a molecule; an isocyanuric ring-containing organosiloxane having an allyl group, an epoxy group, and an organosiloxy group in a molecule; and a catalyst for hydrosilylation reaction has been proposed (see Patent Document 2). A curable silicone composition comprising: an organopolysiloxane having an alkenyl group bonded to a silicon atom; an organohydrogenpolysiloxane having a hydrogen atom bonded to a silicon atom; an adhesion promoter consisting of an isocyanuric acid derivative having an alkoxysilyl group and/or an epoxy group, and a divalent siloxy unit-containing group, and a silane or siloxane compound having an alkoxy group and/or an epoxy group, but having no isocyanuric ring; and a catalyst for hydrosilylation reaction has been proposed (Patent Document 3).

However, there has been a problem in that adhesion to base materials that are in contact even with these curable silicone compositions during curing is not sufficient.

CITATION LIST

Patent Literature

Patent Document 1: Japanese Unexamined Patent Application Publication No. 2010-065161A
Patent Document 2: Japanese Unexamined Patent Application Publication No. 2011-057755A
Patent Document 3: Japanese Unexamined Patent Application Publication No. 2011-208120A

SUMMARY OF INVENTION

Technical Problem

An object of the present invention is to provide a novel organosiloxane, a curable silicone composition that contains the novel organosiloxane as an adhesion promoter and that forms a cured product having excellent adhesion to various base materials, and a semiconductor device that is formed by using the composition and that has excellent reliability.

Solution to Problem

The organosiloxane of the present invention is an organosiloxane represented by the following general formula:

[Chemical Formula 1]

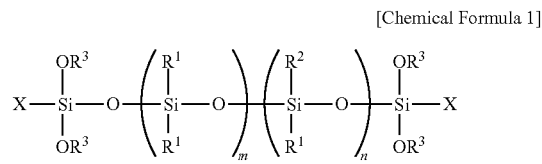

wherein, $R^1$ are the same or different monovalent hydrocarbon groups having from 1 to 12 carbons but having no aliphatic unsaturated bond, $R^2$ is an alkenyl group having from 2 to 12 carbons, $R^3$ are the same or different alkyl groups having from 1 to 3 carbons, X is a group represented by the following general formula:

[Chemical Formula 2]

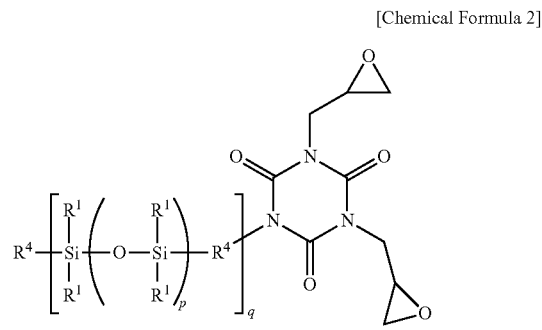

wherein, $R^1$ are the same as those described above, $R^4$ are the same or different alkylene groups, p is an integer of 0 to 50, and q is 0 or 1, wherein m is an integer of 0 to 50, and n is an integer of 1 to 50.

The curable silicone composition of the present invention contains the organosiloxane described above as an adhesion promoter and preferably is cured by hydrosilylation reaction. The curable silicone composition of the present invention more preferably comprises:

(A) 100 parts by mass of an organopolysiloxane having at least two alkenyl groups in a molecule;

(B) an organohydrogenpolysiloxane having at least two silicon atom-bonded hydrogen atoms in a molecule, in an amount such that provides from 0.1 to 10.0 mol of silicon atom-bonded hydrogen atom per 1 mol total of alkenyl group contained in components (A) and (C);

(C) from 0.01 to 50 parts by mass of an adhesion promoter containing the organosiloxane described above; and (D) a catalyst for hydrosilylation reaction, in an amount that is sufficient to promote curing of the present composition.

The semiconductor device of the present invention has a semiconductor element encapsulated with a cured product of the curable silicone composition described above, and preferably, the semiconductor element is a light emitting element.

Effects of Invention

The organosiloxane of the present invention is a novel compound and can impart excellent adhesion to a curable silicone composition. The curable silicone composition of the present invention forms a cured product having excellent adhesion to various base materials that are in contact with the curable silicone composition during curing. Furthermore, the semiconductor device of the present invention has excellent reliability since a semiconductor element is coated with the cured product of the composition.

BRIEF DESCRIPTION OF THE DRAWINGS

FIG. 1 is a cross-sectional view of a light emitting diode (LED) that is an example of a semiconductor device of the present invention.

DETAILED DESCRIPTION OF THE INVENTION

First, the organosiloxane of the present invention will be described in detail.

The organosiloxane of the present invention is represented by the following general formula:

[Chemical Formula 3]

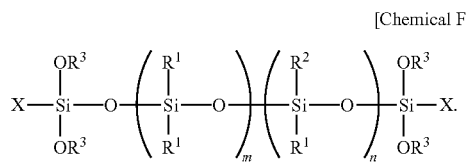

In the formula, $R^1$ are the same or different monovalent hydrocarbon groups having from 1 to 12 carbons but having no aliphatic unsaturated bond. Specific examples thereof include alkyl groups, such as a methyl group, an ethyl group, a propyl group, an isopropyl group, a butyl group, an isobutyl group, a tert-butyl group, a pentyl group, a neopentyl group, a hexyl group, a cyclohexyl group, a heptyl group, an octyl group, a nonyl group, a decyl group, an undecyl group, and a dodecyl group; aryl groups, such as a phenyl group, a tolyl group, a xylyl group, and a naphthyl group; aralkyl groups, such as a benzyl group, a phenethyl group, and a phenylpropyl group; and groups in which some or all of the hydrogen atoms in these groups are substituted with halogen atoms, such as fluorine atoms, chlorine atoms, and bromine atoms. Of these, a methyl group and a phenyl group are preferable.

In the formula, $R^2$ is an alkenyl group having from 2 to 12 carbons. Specific examples thereof include a vinyl group, an allyl group, a butenyl group, a pentenyl group, a hexenyl group, a heptenyl group, an octenyl group, a nonenyl group, a decenyl group, an undecenyl group, and a dodecenyl group. Of these, a vinyl group is preferable.

In the formula, $R^3$ are the same or different alkyl groups having from 1 to 3 carbons. Specific examples thereof include a methyl group, an ethyl group, and a propyl group. Of these, a methyl group is preferable.

In the formula, X is a group represented by the following general formula:

[Chemical Formula 4]

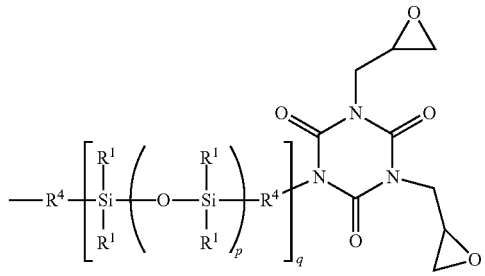

In the formula, $R^1$ are the same or different monovalent hydrocarbon groups having from 1 to 12 carbons but having no aliphatic unsaturated bond, and examples thereof are the same as the groups described above.

In the formula, $R^4$ are the same or different alkylene groups having from 2 to 12 carbons. Specific examples thereof include an ethylene group, a propylene group, a butylene group, a pentylene group, a hexylene group, a heptylene group, an octylene group, a nonylene group, a decylene group, an undecylene group, and a dodecylene group, and preferably are the ethylene group and the propylene group.

In the formula, p is an integer of 0 to 50, preferably an integer of 0 to 30, and more preferably an integer of 0 to 10. Furthermore, in the formula, q is 0 or 1.

In the formula, m is an integer of 0 to 50, preferably an integer of 0 to 30, and more preferably an integer of 0 to 15. Furthermore, in the formula, n is an integer of 1 to 50, preferably an integer of 1 to 30, and more preferably an integer of 1 to 15. Furthermore, m+n is an integer of 2 to 100, preferably an integer of 2 to 50, and more preferably an integer of 2 to 30. This is because, when m is greater than or equal to the upper limit, solubility to the curable silicone composition decreases, and when n is greater than or equal to the lower limit, the adhesion promoter is readily incorporated into the curable silicone composition, and on the other hand, when n is less than or equal to the upper limit, curing is less likely to be inhibited. Furthermore, this is because, when m+n is greater than or equal to the lower limit, solubility to the curable silicone composition is enhanced, and on the other hand, when m+n is less than or equal to the upper limit, handleability is enhanced.

The method of preparing such an organosiloxane is not limited, and examples thereof include a method in which an organosiloxane represented by the following general formula:

[Chemical Formula 5]

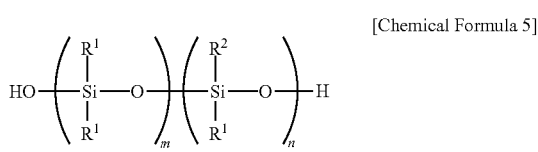

and a compound represented by the following general formula:

[Chemical Formula 6]

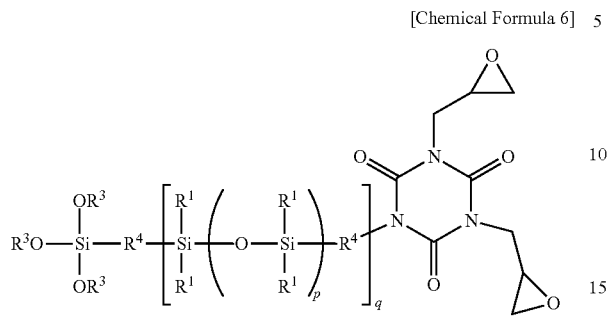

are reacted in the presence of an acid or base catalyst.

In the organosiloxane described above, $R^1$ in the formula are the same or different monovalent hydrocarbon groups having from 1 to 12 carbons but having no aliphatic unsaturated bond, and examples thereof are the same as the groups described above. Furthermore, in the formula, $R^2$ is an alkenyl group having from 2 to 12 carbons, and examples thereof are the same as the groups described above. Furthermore, in the formula, m and n are integers that are the same as the integers described above.

The following compounds are examples of such organosiloxanes. Note that, in the formulas, m' is an integer of 1 to 50, and n is an integer of 1 to 50.

[Chemical Formula 7]

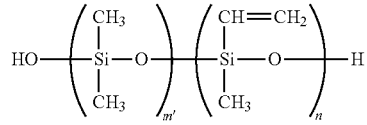

[Chemical Formula 8]

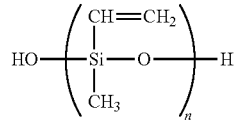

[Chemical Formula 9]

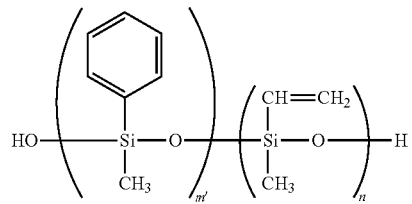

Furthermore, in the composition described above, in the formula, $R^1$ are the same or different monovalent hydrocarbon groups having from 1 to 12 carbons but having no aliphatic unsaturated bond, and examples thereof are the same as the groups described above. Furthermore, in the formula, $R^3$ are the same or different alkyl groups having from 1 to 3 carbons, and examples thereof are the same as the groups described above. Furthermore, in the formula, $R^4$ are the same or different alkylene groups having from 2 to 12 carbons, and examples thereof are the same as the groups described above. Furthermore, in the formula, p is an integer that is the same as the integer described above, and q is 0 or 1.

The following compound is an example of such compounds.

[Chemical Formula 10]

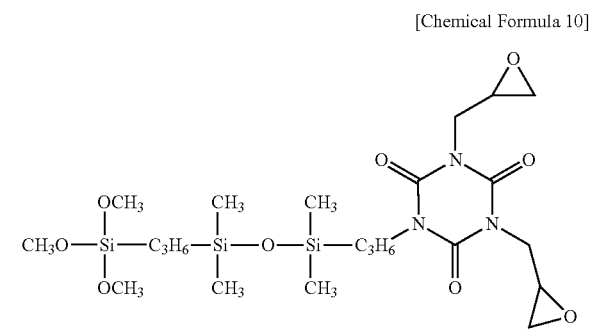

In the preparation method described above, the compound described above needs to be reacted with the organosiloxane described above in an amount that the compound is at least 1 mol to 2 mol per 1 mol of the organosiloxane. This is because, when the amount of the compound is greater than or equal to the lower limit of the range described above, the resulting organosiloxane can impart sufficient adhesion to the curable silicone composition, and on the other hand, when the amount of the compound is less than or equal to the upper limit of the range described above, the resulting organosiloxane reacts with the silicon atom-bonded hydrogen atom in the hydrosilylation curable silicone composition and can enhance transmittance of the resulting cured product.

Examples of the acid used in the preparation method described above include hydrochloric acid, acetic acid, formic acid, nitric acid, oxalic acid, sulfuric acid, phosphoric acid, polyphosphoric acid, polycarboxylic acid, trifluoromethane sulfonic acid, and ion exchange resins. Furthermore, examples of the alkali used in the preparation method described above include inorganic alkalis, such as potassium hydroxide, sodium hydroxide, calcium hydroxide, and magnesium hydroxide; and organic base compounds, such as triethylamine, diethylamine, monoethanolamine, diethanolamine, triethanolamine, ammonia water, tetramethylammonium hydroxide, alkoxysilanes having an amino group, aminopropyltrimethoxysilane, sodium silanolate, and potassium silanolate.

An organic solvent may be used in the preparation method described above. The utilized organic solvent is exemplified by ethers, ketones, acetates, aromatic or aliphatic hydrocarbons, and a γ-butyrolactone; and mixtures of two or more types of such solvents. Preferred organic solvents are exemplified by propylene glycol monomethyl ether, propylene glycol monomethyl ether acetate, propylene glycol monoethyl ether, propylene glycol monopropyl ether, propylene glycol monobutyl ether, propylene glycol mono-t-butyl ether, γ-butyrolactone, toluene, and xylene.

In the preparation method described above, when an organic solvent is used and this reaction is promoted by heating, the reaction is preferably performed at the reflux temperature of the organic solvent.

Next, a curable silicone composition of the present invention will be described.

The curable silicone composition of the present invention contains the organosiloxane described above as an adhesion promoter. The curing mechanism of such a curable silicone composition is not limited, and examples thereof include hydrosilylation reactions, condensation reactions, and radical reactions, and hydrosilylation reactions are preferable. The hydrosilylation curable silicone composition preferably comprises:

(A) 100 parts by mass of an organopolysiloxane having at least two alkenyl groups in a molecule;

(B) an organohydrogenpolysiloxane having at least two silicon atom-bonded hydrogen atoms in a molecule, in an amount such that provides from 0.1 to 10 mol of silicon atom-bonded hydrogen atom per 1 mol total of alkenyl groups contained in components (A) and (C);

(C) from 0.01 to 50 parts by mass of an adhesion promoter containing the organosiloxane described above; and (D) a catalyst for hydrosilylation reaction.

Component (A) is the base compound of the present composition and is an organopolysiloxane having at least two alkenyl groups in a molecule. Examples of the alkenyl groups in component (A) include alkenyl groups having from 2 to 12 carbons, such as a vinyl group, an allyl group, a butenyl group, a pentenyl group, a hexenyl group, a heptenyl group, an octenyl group, a nonenyl group, a decenyl group, an undecenyl group, and a dodecenyl group. Of these, a vinyl group is preferable. Furthermore, examples of the group bonded to the silicon atom other than alkenyl groups in component (A) include alkyl groups having from 1 to 12 carbons, such as a methyl group, an ethyl group, a propyl group, an isopropyl group, a butyl group, an isobutyl group, a tert-butyl group, a pentyl group, a neopentyl group, a hexyl group, a cyclohexyl group, a heptyl group, an octyl group, a nonyl group, a decyl group, an undecyl group, and a dodecyl group; aryl groups having from 6 to 20 carbons, such as a phenyl group, a tolyl group, a xylyl group, and a naphthyl group; aralkyl groups having from 7 to 20 carbons, such as a benzyl group, a phenethyl group, and a phenylpropyl group; and groups in which some or all of the hydrogen atoms in these groups are substituted with halogen atoms, such as fluorine atoms, chlorine atoms, and bromine atoms. Note that the silicon atom in component (A) may have a small amount of a hydroxy group and/or an alkoxy group, such as a methoxy group and an ethoxy group, at levels that do not impair the object of the present invention.

The molecular structure of component (A) is not particularly limited, and examples thereof include straight, partially branched straight, branched, cyclic, and three-dimensional network structures. Component (A) may be one type of organopolysiloxane having such a molecular structure, or may be a mixture of two or more types of organopolysiloxanes having such molecular structures.

The state of component (A) at 25° C. is not limited and, for example, may be liquid or solid. When component (A) is liquid, the viscosity at 25° C. is preferably in a range of 1 to 1,000,000 mPa·s, and particularly preferably in a range of 10 to 1,000,000 mPa·s. Note that this viscosity can be determined by, for example, measurement using a B type viscometer in accordance with JIS K 7117-1.

Examples of component (A) include dimethylpolysiloxane capped at both molecular terminals with dimethylvinylsiloxy groups, dimethylsiloxane-methylvinylsiloxane copolymers capped at both molecular terminals with dimethylvinylsiloxy groups, dimethylsiloxane-methylphenylsiloxane copolymers capped at both molecular terminals with dimethylvinylsiloxy groups, methylphenylpolysiloxane capped at both molecular terminals with dimethylvinylsiloxy groups, dimethylsiloxane-methylvinylsiloxane copolymers capped at both molecular terminals with trimethylsiloxy groups, dimethylsiloxane-methylvinylsiloxane-methylphenylsiloxane copolymers capped at both molecular terminals with trimethylsiloxy groups, copolymers comprising $(CH_3)_3SiO_{1/2}$ units, $(CH_3)_2(CH_2\!=\!CH)SiO_{1/2}$ units, and $SiO_{4/2}$ units, copolymers comprising $(CH_3)_2(CH_2\!=\!CH)SiO_{1/2}$ units and $SiO_{4/2}$ units, and the following organopolysiloxanes. Note that, in the formulas, Me represents a methyl group, Vi represents a vinyl group, Ph represents a phenyl group, and x and x' are each independently an integer of 1 to 5,000.

$ViMe_2SiO(Me_2SiO)_xSiMe_2Vi$
$ViPhMeSiO(Me_2SiO)_xSiMePhVi$
$ViPh_2SiO(Me_2SiO)_xSiPh_2Vi$
$ViMe_2SiO(Me_2SiO)_x(Ph_2SiO)_{x'}SiMe_2Vi$
$ViPhMeSiO(Me_2SiO)_x(Ph_2SiO)_{x'}SiPhMeVi$
$ViPh_2SiO(Me_2SiO)_x(Ph_2SiO)_{x'}SiPh_2Vi$
$ViMe_2SiO(MePhSiO)_xSiMe_2Vi$
$MePhViSiO(MePhSiO)_xSiMePhVi$
$Ph_2ViSiO(MePhSiO)_xSiPh_2Vi$
$ViMe_2SiO(Ph_2SiO)_x(PhMeSiO)_{x'}SiMe_2Vi$
$ViPhMeSiO(Ph_2SiO)_x(PhMeSiO)_{x'}SiPhMeVi$
$ViPh_2SiO(Ph_2SiO)_x(PhMeSiO)_{x'}SiPh_2Vi$

Component (B) is a crosslinking agent of the present composition and is an organopolysiloxane having at least two silicon atom-bonded hydrogen atoms in a molecule. Examples of the molecular structure of component (B) include straight, partially branched straight, branched, cyclic, and dendritic structures. Of these, straight, partially branched straight, and dendritic structures are preferable. The bonding positions of the silicon atom-bonded hydrogen atoms in component (B) are not limited, and examples thereof include a molecular terminal(s) and/or side chain(s). Furthermore, examples of the silicon atom-bonded group other than the silicon atom-bonded hydrogen atom in component (B) include alkyl groups, such as a methyl group, an ethyl group, and a propyl group; aryl groups, such as a phenyl group, a tolyl group, and a xylyl group; aralkyl groups, such as a benzyl group and a phenethyl group; and halogenated alkyl groups, such as a 3-chloropropyl group and a 3,3,3-trifluoropropyl group; and the methyl group and the phenyl group are preferable. Furthermore, although the viscosity of component (B) is not limited, the viscosity at 25° C. is preferably in a range of 1 to 10,000 mPa·s, and particularly preferably in a range of 1 to 1,000 mPa·s.

Examples of component (B) include 1,1,3,3-tetramethyldisiloxane, 1,3,5,7-tetramethylcyclotetrasiloxane, tris(dimethylhydrogensiloxy)methylsilane, tris(dimethylhydrogensiloxy)phenylsilane, 1-glycidoxypropyl-1,3,5,7-tetramethylcyclotetrasiloxane, 1,5diglycidoxypropyl-1,3,5,7-tetramethylcyclotetrasiloxane, 1-glycidoxypropyl-5-trimethoxysilylethyl-1,3,5,7-tetramethylcyclotetrasiloxane, methylhydrogenpolysiloxane capped at both molecular terminals with trimethylsiloxy groups, dimethylsiloxane-methylhydrogensiloxane copolymers capped at both molecular terminals with trimethylsiloxy groups, dimethylpolysiloxane capped at both molecular terminals with dimethylhydrogensiloxy groups, dimethylsiloxane-methylhydrogensiloxane copolymers capped at both molecular terminals with dimethylhydrogensiloxy groups, methylhydrogensiloxane-diphenylsiloxane copolymers capped at both molecular terminals with trimethylsiloxy groups, methylhydrogensiloxane-diphenylsiloxane-dimethylsiloxane copolymers capped at both molecular terminals with trimethylsiloxy groups, hydrolysis condensates of trimethoxysilane, copolymers comprising $(CH_3)_2HSiO_{1/2}$ units and $SiO_{4/2}$ units, copolymers comprising $(CH_3)_2HSiO_{1/2}$ units, $SiO_{4/2}$ units, and $(C_6H_5)SiO_{3/2}$ units, and the following organohydrogenpolysiloxane. Note that, in the formulas, Me represents a methyl group, Vi represents a vinyl group, Ph represents a phenyl group, Naph represents a naphthyl group, and y and y' are each independently an integer of 1 to 100, c, d, e, and f are each independently a positive number but the total of c, d, e, and f is 1.

HMe$_2$SiO(Ph$_2$SiO)$_y$SiMe$_2$H
HMePhSiO(Ph$_2$SiO)$_y$SiMePhH
HMeNaphSiO(Ph$_2$SiO)$_y$SiMeNaphH
HMePhSiO(Ph$_2$SiO)$_y$(MePhSiO)$_y$SiMePhH
HMePhSiO(Ph$_2$SiO)$_y$(Me$_2$SiO)$_y$SiMePhH
(HMe$_2$SiO$_{1/2}$)$_c$(PhSiO$_{3/2}$)$_d$
(HMePhSiO$_{1/2}$)$_c$(PhSiO$_{3/2}$)$_d$
(HMePhSiO$_{1/2}$)$_c$(NaphSiO$_{3/2}$)$_d$
(HMe$_2$SiO$_{1/2}$)$_c$(NaphSiO$_{3/2}$)$_d$
(HMePhSiO$_{1/2}$)$_c$(HMe$_2$SiO$_{1/2}$)$_d$(PhSiO$_{3/2}$)$_e$
(HMe$_2$SiO$_{1/2}$)$_c$(Ph$_2$SiO$_{2/2}$)$_d$(PhSiO$_{3/2}$)$_e$
(HMePhSiO$_{1/2}$)$_c$(Ph$_2$SiO$_{2/2}$)$_d$(PhSiO$_{3/2}$)$_e$
(HMe$_2$SiO$_{1/2}$)$_c$(Ph$_2$SiO$_{2/2}$)$_d$(NaphSiO$_{3/2}$)$_e$
(HMePhSiO$_{1/2}$)$_c$(Ph$_2$SiO$_{2/2}$)$_d$(NaphSiO$_{3/2}$)$_e$
(HMePhSiO$_{1/2}$)$_c$(HMe$_2$SiO$_{1/2}$)$_d$(NaphSiO$_{3/2}$)$_e$
(HMePhSiO$_{1/2}$)$_c$(HMe$_2$SiO$_{1/2}$)$_d$(Ph$_2$SiO$_{2/2}$)$_e$(NaphSiO$_{3/2}$)$_f$
(HMePhSiO$_{1/2}$)$_c$(HMe$_2$SiO$_{1/2}$)$_d$(Ph$_2$SiO$_{2/2}$)$_e$(PhSiO$_{3/2}$)$_f$ The content of component (B) is an amount such that the amount of the silicon atom-bonded hydrogen atom in this component is from 0.1 to 10 mol, and preferably from 0.5 to 5 mol, per 1 mol total of alkenyl groups contained in components (A) and (C). This is because, when the content of component (B) is less than or equal to the upper limit of the range described above, excellent mechanical characteristics of the resulting cured product is achieved, and on the other hand, when the content of component (B) is greater than or equal to the lower limit of the range described above, excellent curability of the resulting composition is achieved.

Component (C) is an adhesion promoter for imparting adhesion to the present composition. Component (C) is as described above. The content of component (C) is in a range of 0.01 to 50 parts by mass, and preferably in a range of 0.1 to 20 parts by mass, per 100 parts by mass of component (A). This is because, when the content of component (C) is greater than or equal to the lower limit of the range described above, sufficient adhesion can be imparted to the resulting composition, and on the other hand, when the content of component (C) is less than or equal to the upper limit of the range described above, curability of the resulting composition is less likely to be deteriorated and coloring or the like of the resulting cured product can be suppressed.

Component (D) is a catalyst for hydrosilylation reaction for accelerating the curing of the present composition, and examples thereof include platinum-based catalysts, rhodium-based catalysts, and palladium-based catalysts. Particularly, component (D) is preferably a platinum-based catalyst so that the curing of the present composition can be dramatically accelerated. Examples of the platinum-based catalyst include a platinum fine powder, chloroplatinic acid, an alcohol solution of chloroplatinic acid, a platinum-alkenylsiloxane complex, a platinum-olefin complex and a platinum-carbonyl complex, and the platinum-alkenylsiloxane complex is preferred.

The content of component (D) is an effective amount for accelerating the curing of the present composition. Specifically, in order to be able to sufficiently accelerate the curing reaction of this composition, the content of component (D) is preferably in an amount so that the catalyst metal in component (D) is, in terms of a mass unit, in a range of 0.01 to 500 ppm, more preferably in a range of 0.01 to 100 ppm, and particularly preferably in a range of 0.01 to 50 ppm, relative to the amount of the present composition.

Furthermore, the present composition may contain (E) a hydrosilylation reaction inhibitor, as an optional component, such as alkyne alcohols, such as 2-methyl-3-butyn-2-ol, 3,5-dimethyl-1-hexyn-3-ol, and 2-phenyl-3-butyn-2-ol; ene-yne compounds, such as 3-methyl-3-penten-1-yne and 3,5-dimethyl-3-hexen-1-yne; and 1,3,5,7-tetramethyl-1,3,5,7-tetravinylcyclotetrasiloxane, 1,3,5,7-tetramethyl-1,3,5,7-tetrahexenylcyclotetrasiloxane, and benzotriazole. In the present composition, although the content of component (E) is not limited, the content of component (E) is preferably in a range of 0.0001 to 5 parts by mass, per 100 parts by mass total of components (A) to (D).

Furthermore, the present composition may also contain an adhesion promoter other than component (C) to enhance the adhesion of the cured product to a base material which is in contact with the present composition during the curing. As this adhesion promoter, an organosilicon compound having at least one alkoxy group bonded to a silicon atom in a molecule is preferable. This alkoxy group is exemplified by a methoxy group, an ethoxy group, a propoxy group, a butoxy group, and a methoxyethoxy group; and the methoxy group is particularly preferred. Furthermore, examples of other groups, excluding the alkoxy group bonded to the silicon atom of the organosilicon compound, include substituted or unsubstituted monovalent hydrocarbon groups, such as an alkyl group, an alkenyl group, an aryl group, an aralkyl group, and a halogenated alkyl group; glycidoxyalkyl groups, such as a 3-glycidoxypropyl group and a 4-glycidoxybutyl group; epoxycyclohexylalkyl groups, such as a 2-(3,4-epoxycyclohexyl)ethyl group and a 3-(3,4-epoxycyclohexyl)propyl group; epoxyalkyl groups, such as a 3,4-epoxybutyl group and a 7,8-epoxyoctyl group; acrylic group-containing monovalent organic groups, such as a 3-methacryloxypropyl group; and a hydrogen atom. This organosilicon compound preferably has a silicon-bonded alkenyl group or silicon-bonded hydrogen atom. Examples of such an organosilicon compound include organosilane compounds, organosiloxane oligomers, and alkyl silicates. Examples of the molecular structure of the organosiloxane oligomer or alkyl silicate include straight, partially branched straight, branched, cyclic, and net-shaped structures. Straight, branched, and net-shaped structures are particularly preferred. Examples of such an organosilicon compound include silane compounds such as 3-glycidoxypropyl trimethoxysilane, 2-(3,4-epoxycyclohexyl)ethyl trimethoxysilane, and 3-methacryloxypropyl trimethoxysilane; siloxane compounds having at least one of silicon-bonded alkenyl groups and silicon-bonded hydrogen atoms, and at least one silicon-bonded alkoxy group in a molecule; mixtures of a silane compound or siloxane compound having at least one silicon-bonded alkoxy group and a siloxane compound having at least one silicon-bonded hydroxyl group and at least one silicon-bonded alkenyl group in a molecule; and methyl polysilicate, ethyl polysilicate, and epoxy group-containing ethyl polysilicate.

Furthermore, the present composition may contain a phosphor that is used to obtain light of a desired wavelength by converting the wavelength of light emitted from a light emitting element that is encapsulated or covered with the cured product of the present composition. Examples of such a phosphor include yellow, red, green, and blue light emitting phosphors formed from oxide phosphors, oxynitride phosphors, nitride phosphors, sulfide phosphors, oxysulfide phosphors, or the like, which are widely used in light emitting diodes (LEDs). Examples of the oxide-based phosphors include yttrium, aluminum, and garnet-type YAG green to yellow light-emitting phosphors containing cerium ions; terbium, aluminum, and garnet-type TAG yellow light-emitting phosphors containing cerium ions; and silicate green to yellow light-emitting phosphors containing cerium or europium ions. Examples of the oxynitride-based phosphors include silicon, aluminum, oxygen, and nitrogen-type SiALON red to green light-emitting phosphors containing europium ions. Examples of the nitride-based phosphors include calcium, strontium, aluminum, silicon, and nitrogen-type CASN red light-emitting phosphors containing europium ions. Examples of the sulfide-based phosphors include ZnS green light-emitting phosphors containing copper ions or aluminum ions. Examples of the oxysulfide-based phosphors include $Y_2O_2S$ red light-emitting phosphors containing europium ions. One type of these phosphors or a mixture of two or more types of these phosphors may be used. In the present composition, the content of the phosphor is in a range of 0.1 to 70 mass %, and preferably in a range of 1 to 20 mass %, relative to the total amount of components (A) to (D).

Moreover, an inorganic filler such as silica, glass, alumina or zinc oxide; an organic resin fine powder of a polymethacrylate resin and the like; a heat-resistant agent, a dye, a pigment, a flame retardant, a solvent and the like may be incorporated as optional components in the present composition at levels that do not impair the object of the present invention.

To sufficiently suppress the discoloration of silver electrodes or silver plating of a substrate in an optical semiconductor device due to sulfur-containing gas in the air, the present composition may contain at least one type of a fine powder having an average particle diameter of 0.1 nm to 5 μm selected from the group consisting of zinc oxide fine powders surface-coated with at least one type of oxide of an element selected from the group consisting of Al, Ag, Cu, Fe, Sb, Si, Sn, Ti, Zr, and rare earth elements, zinc oxide fine powders surface-treated with organosilicon compounds having no alkenyl groups, and hydrate fine powders of zinc carbonate.

In a zinc oxide fine powder surface-coated with an oxide, examples of the rare earth elements include yttrium, cerium, and europium. Examples of the oxide on the surface of the zinc oxide fine powder include $Al_2O_3$, $AgO$, $Ag_2O$, $Ag_2O_3$, $CuO$, $Cu_2O$, $FeO$, $Fe_2O_3$, $Fe_3O_4$, $Sb_2O_3$, $SiO_2$, $SnO_2$, $Ti_2O_3$, $TiO_2$, $Ti_3O_5$, $ZrO_2$, $Y_2O_3$, $CeO_2$, $Eu_2O_3$, and mixtures of two or more types of these oxides.

In a zinc oxide fine powder surface-treated with an organic silicon compound, the organic silicon compound does not have alkenyl groups, and examples thereof include organosilanes, organosilazanes, polymethylsiloxanes, organohydrogenpolysiloxanes, and organosiloxane oligomers. Specific examples include organochlorosilanes, such as trimethylchlorosilane, dimethylchlorosilane, and methyltrichlorosilane; organotrialkoxysilanes, such as methyltrimethoxysilane, methyltriethoxysilane, phenyltrimethoxysilane, ethyltrimethoxysilane, n-propyltrimethoxysilane, and γ-methacryloxypropyltrimethoxysilane; diorganodialkoxysilanes, such as dimethyldimethoxysilane, dimethyldiethoxysilane, and diphenyldimethoxysilane; triorganoalkoxysilanes, such as trimethylmethoxysilane and trimethylethoxysilane; partial condensates of these organoalkoxysilanes; organosilazanes, such as hexamethyldisilazane; and a polymethylsiloxane, an organohydrogenpolysiloxane, an organosiloxane oligomer having a silanol group or an alkoxy group, and silanol group- or alkoxy group-containing resin-like organopolysiloxanes comprising an $R^8SiO_{3/2}$ unit (in the formula, $R^8$ is a monovalent hydrocarbon group that is not an alkenyl group and that is exemplified by alkyl groups, such as a methyl group, an ethyl group, and a propyl group; and aryl groups, such as a phenyl group) and/or an $SiO_{4/2}$ unit.

In addition, the composition may also contain a triazole-based compound as an optional component in order to enable the further suppression of the discoloration of the silver electrodes or the silver plating of the substrate due to a sulfur-containing gas in the air. Specific examples thereof include 1H-1,2,3-triazole, 2H-1,2,3-triazole, 1H-1,2,4-triazole, 4H-1,2,4-triazole, 2-(2'-hydroxy-5'-methylphenyl)benzotriazole, 1H-1,2,3-triazole, 2H-1,2,3-triazole, 1H-1,2,4-triazole, 4H-1,2,4-triazole, benzotriazole, tolyltriazole, carboxybenzotriazole, 1H-benzotriazole-5-methylcarboxylate, 3-amino-1,2,4-triazole, 4-amino-1,2,4-triazole, 5-amino-1,2,4-triazole, 3-mercapto-1,2,4-triazole, chlorobenzotriazole, nitrobenzotriazole, aminobenzotriazole, cyclohexano[1,2-d]triazole, 4,5,6,7-tetrahydroxytolyltriazole, 1-hydroxybenzotriazole, ethylbenzotriazole, naphthotriazole, 1-N,N-bis(2-ethylhexyl)-[(1,2,4-triazol-1-yl)methyl]amine, 1-[N,N-bis(2-ethylhexyl)aminomethyl]benzotriazole, 1-[N,N-bis(2-ethylhexyl)aminomethyl]tolyltriazole, 1-[N,N-bis(2-ethylhexyl)aminomethyl]carboxybenzotriazole, 1-[N,N-bis(2-hydroxyethyl)-aminomethyl]benzotriazole, 1-[N,N-bis(2-hydroxyethyl)-aminomethyl]tolyltriazole, 1-[N,N-bis(2-hydroxyethyl)-aminomethyl]carboxybenzotriazole, 1-[N,N-bis(2-hydroxypropyl)aminomethyl]carboxybenzotriazole, 1-[N,N-bis(1-butyl)aminomethyl]carboxybenzotriazole, 1-[N,N-bis(1-octyl)aminomethyl]carboxybenzotriazole, 1-(2',3'-dihydroxypropyl)benzotriazole, 1-(2',3'-di-carboxyethyl)benzotriazole, 2-(2'-hydroxy-3',5'-di-tert-butylphenyl)benzotriazole, 2-(2'-hydroxy-3',5'-aminophenyl)benzotriazole, 2-(2'-hydroxy-4'-octoxyphenyl)benzotriazole, 2-(2'-hydroxy-5'-tert-butylphenyl)benzotriazole, 1-hydroxybenzotriazole-6-carboxylic acid, 1-oleoylbenzotriazole, 1,2,4-triazol-3-ol, 5-amino-3-mercapto-1,2,4-triazole, 5-amino-1,2,4-triazole-3-carboxylic acid, 1,2,4-triazole-3-carboxyamide, 4-aminourazole, and 1,2,4-triazol-5-one. The content of the triazole-based compound is not particularly limited; however, the content is, in terms of a mass unit, in a range of 0.01 ppm to 3%, and preferably in a range of 0.1 ppm to 1%, relative to the amount of the present composition.

The present composition may further contain a cerium-containing organopolysiloxane as an optional component to suppress cracking due to heat aging of the resulting cured product. The cerium-containing organopolysiloxane can be prepared by, for example, a reaction between cerium chloride or a ceric salt of carboxylic acid and an alkali metal salt of silanol group-containing organopolysiloxane.

Examples of the ceric salt of carboxylic acid include cerium 2-ethylhexanoate, cerium naphthenate, cerium oleate, cerium laurate, and cerium stearate.

Furthermore, examples of the alkali metal salt of silanol group-containing organopolysiloxane include potassium salts of diorganopolysiloxane capped at both molecular terminals with silanol groups, sodium salts of diorganopolysiloxane capped at both molecular terminals with silanol groups, potassium salts of diorganopolysiloxane capped at one molecular terminal with a silanol group and the other molecular terminal with triorganosiloxy group, and sodium salts of diorganopolysiloxane capped at one molecular terminal with a silanol group and the other molecular terminal with triorganosiloxy group. Note that examples of the group to be bonded to the silicon atom in this organopolysiloxane include alkyl groups having from 1 to 12 carbons, such as a methyl group, an ethyl group, a propyl group, an isopropyl group, an n-butyl group, an isobutyl group, a tert-butyl group, an n-pentyl group, a neopentyl group, a hexyl group, a cyclohexyl group, a heptyl group, an octyl group, a nonyl group, a decyl group, an undecyl group, and a dodecyl group; aryl groups having from 6 to 20 carbons, such as a phenyl group, a tolyl group, a xylyl group, and a naphthyl group; aralkyl groups having from 7 to 20 carbons, such as a benzyl group, a phenethyl group, and a phenylpropyl group; and groups in which some or all of the hydrogen atoms in these groups are substituted with halogen atoms, such as fluorine atoms, chlorine atoms, and bromine atoms.

The reaction described above is performed at room temperature or by heating in an organic solvent including alcohols, such as methanol, ethanol, isopropanol, and butanol; aromatic hydrocarbons, such as toluene and xylene; aliphatic hydrocarbons, such as hexane and heptane; mineral spirit, ligroin, petroleum ether, and the like. Furthermore, the resulting reaction product is preferably subjected to removal of organic solvents and/or low boiling point components by distillation and/or removal of precipitates by filtration, as necessary. Furthermore, to accelerate this reaction, dialkylformamide, hexaalkylphosphoramide, or the like may be added. The content of the cerium atom in the cerium-containing organopolysiloxane prepared as described above is preferably in a range of 0.1 to 5 mass %.

Although the content of the cerium-containing organopolysiloxane is not limited, the content is preferably in an amount by which the content of the cerium atom, in terms of a mass unit, is in a range of 10 to 2,000 ppm, 20 to 2,000 ppm, 20 to 1,000 ppm, or 20 to 500 ppm, relative to the amount of the present composition. This is because, when the content of the cerium-containing organopolysiloxane is greater than or equal to the lower limit of the range described above, heat resistance of the resulting cured product can be enhanced, and on the other hand, when the content is less than or equal to the upper limit of the range described above, variation in luminescent chromaticity can be decreased when the composition is used in an optical semiconductor device.

The curing of the present composition proceeds either at room temperature or under heating, but it is preferable to heat the composition in order to achieve rapid curing. The heating temperature is preferably in a range of 50 to 200° C.

The semiconductor device of the present invention will now be described in detail.

The semiconductor device of the present invention is produced by encapsulating a semiconductor element with a cured product of the curable silicone composition described above. Examples of such a semiconductor device of the present invention include a light emitting diode (LED), a photocoupler, and a charge coupled device (CCD). Examples of the semiconductor element include a light emitting diode (LED) chip and a solid-state image sensing device.

FIG. 1 illustrates a cross-sectional view of a single surface mounted type LED, which is one example of the semiconductor device of the present invention. In the LED illustrated in FIG. 1, a light emitting element (LED chip) 1 is die-bonded to a lead frame 2, and the light emitting element (LED chip) 1 and a lead frame 3 are wire-bonded by a bonding wire 4. A frame 5 is provided around the periphery of this light emitting element (LED chip) 1, and the light emitting element (LED chip) 1 on the inner side of this frame 5 is encapsulated with a cured product 6 of the curable silicone composition of the present invention.

An example of a method for producing the surface mounted type LED illustrated in FIG. 1 is a method including die-bonding the light emitting element (LED chip) 1 to the lead frame 2, wire-bonding this light emitting element (LED chip) 1 and the lead frame 3 by means of the gold bonding wire 4, charging the curable silicone composition of the present invention inside the frame 5 provided around the periphery of the light emitting element (LED chip) 1, and then curing the curable silicone composition by heating at 50 to 200° C.

EXAMPLES

The organosiloxane, the curable silicone composition, and the semiconductor device of the present invention will be described in detail using examples. Note that, in the formulas, Me represents a methyl group, Vi represents a vinyl group, Ph represents a phenyl group, and Ep represents a 3-glycidoxypropyl group.

Reference Example 1

First, 400 g (2.02 mol) of phenyltrimethoxysilane and 93.5 g (0.30 mol) of 1,3-divinyl-1,3-diphenyldimethyldisiloxane were loaded into a reaction vessel and mixed in advance. Next, 1.74 g (11.6 mmol) of trifluoromethane sulfonic acid was added, and 110 g (6.1 mol) of water was added and heat-refluxed for 2 hours while stirring. Next, the mixture was distilled at atmospheric pressure by heating until the temperature reached 85° C. Next, 89 g of toluene and 1.18 g (21.1 mmol) of potassium hydroxide were added, and the mixture was distilled at atmospheric pressure by heating until the reaction temperature reached 120° C. and then allowed to react at this temperature for 6 hours. The mixture was then cooled to room temperature, and the cooled mixture was neutralized by adding 0.68 g (11.4 mmol) of acetic acid. After filtering off the formed salts, low boiling point substances were removed from the obtained transparent solution by heating under reduced pressure to prepare 347 g (yield: 98%) of an organopolysiloxane resin represented by the following average unit formula:

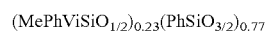

$(MePhViSiO_{1/2})_{0.23}(PhSiO_{3/2})_{0.77}$

Example 1

In a reaction vessel, 190 g of organosiloxane represented by the following average formula:

[Chemical Formula 11]

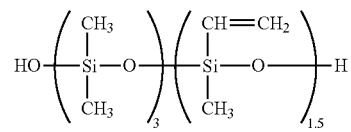

598 g of a compound represented by the following formula:

[Chemical Formula 12]

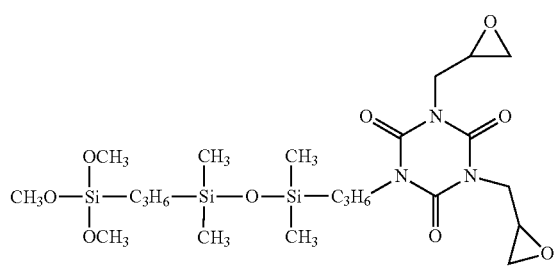

and 0.23 g of potassium silanolate were charged and heated at 120 to 130° C. for 6 hours to obtain a light yellow liquid. As a result of NMR analysis, it was found that this liquid was an organosiloxane represented by the following average formula:

[Chemical Formula 13]

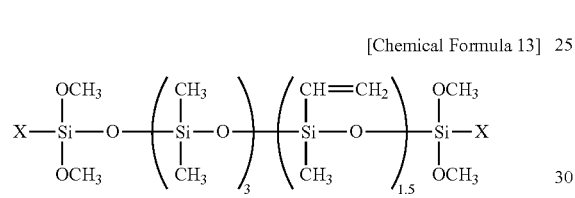

in the formula, X is a group represented by formula:

[Chemical Formula 14]

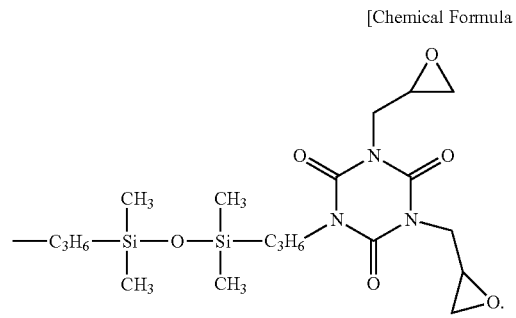

Example 2

In a reaction vessel, 26 g of organosiloxane represented by the following formula:

[Chemical Formula 15]

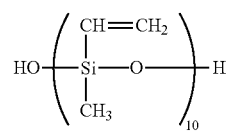

30 g of a compound represented by the following formula:

[Chemical Formula 16]

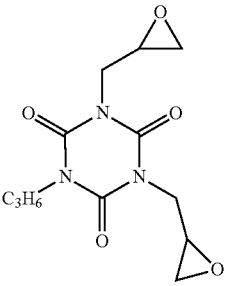

and 1.7 g of calcium hydroxide were charged and heated at 100° C. for 6 hours to obtain a light yellow liquid. As a result of NMR analysis, it was found that this liquid was an organosiloxane represented by the following average formula:

[Chemical Formula 17]

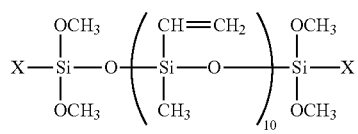

in the formula, X is a group represented by the following formula:

[Chemical Formula 18]

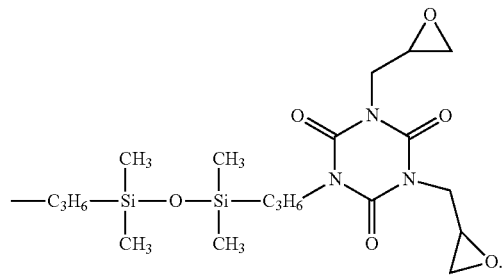

Example 3

In a reaction vessel, 10 g of organosiloxane represented by the following formula:

[Chemical Formula 19]

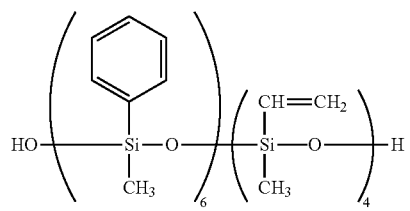

9.8 g of a compound represented by the following formula:

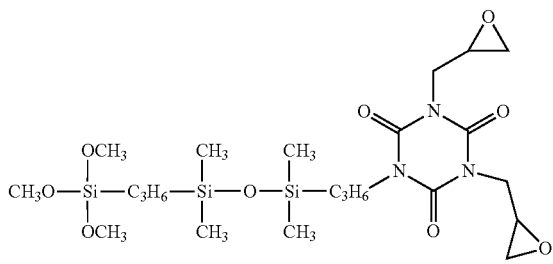

and 1.1 g of calcium hydroxide were charged and heated at 120 to 130° C. for 6 hours to obtain a light yellow liquid. As a result of NMR analysis, it was found that this liquid was an organosiloxane represented by the following average formula:

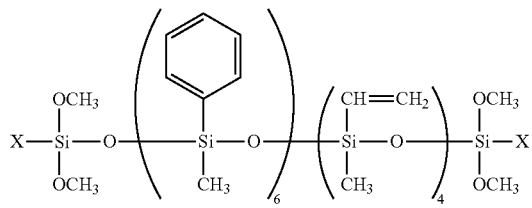

in the formula, X is a group represented by the following formula:

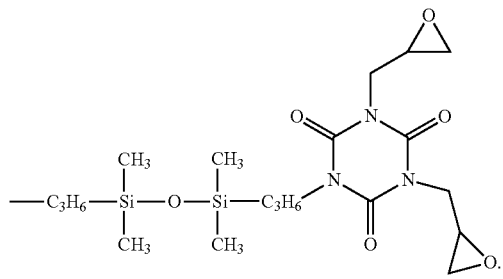

Examples 4 to 8 and Comparative Examples 1 to 3

The curable silicone compositions shown in Table 1 were prepared using the components described below. Moreover, in Table 1, the content of component (D) is expressed in terms of the content (ppm; in terms of a mass unit) of platinum metal relative to the amount of the curable silicone composition. Furthermore, SiH/Vi in Table 1 shows the number of moles of silicon atom-bonded hydrogen atom in component (B) per 1 mol total of alkenyl groups contained in components (A) and (C).

The following components were used as component (A).

Component (A-1): an organopolysiloxane represented by the following average unit formula:

$(Me_2ViSiO_{1/2})_{0.2}(PhSiO_{3/2})_{0.8}$

Component (A-2): an organopolysiloxane prepared in Reference Example 1 and represented by the following average unit formula:

$(MePhViSiO_{1/2})_{0.23}(PhSiO_{3/2})_{0.77}$

Component (A-3): a methylphenylpolysiloxane capped at both molecular terminals with dimethylvinylsiloxy groups, and having a viscosity of 3,000 mPa·s.

The following components were used as component (B).

Component (B-1): an organotrisiloxane represented by the following formula:

$HMe_2SiOPh_2SiOSiMe_2H$

The following components were used as component (C).

Component (C-1): an adhesion promoter comprising the organosiloxane prepared in Example 1

Component (C-2): an adhesion promoter comprising the organosiloxane prepared in Example 2

Component (C-3): an adhesion promoter comprising the organosiloxane prepared in Example 3

Component (C-4): an adhesion promoter comprising a condensation reaction product of a methylvinylsiloxane oligomer capped at both molecular terminals with silanol groups, and having a viscosity at 25° C. of 30 mPa·s, and 3-glycidoxypropyltrimethoxysilane The following components were used as component (D).

Component (D-1): a solution of a platinum-1,3-divinyl-1,1,3,3-tetramethyldisiloxane complex in 1,3,5,7-tetramethyl-1,3,5,7-tetravinylcyclotetrasiloxane (the solution contains 0.1 mass % of platinum)

Adhesive strength of the cured product of the curable silicone composition was measured as follows.

Adhesive Strength

A spacer that was made of a fluoro resin and had a thickness of 2 mm and a hole having a diameter of 5 mm was placed on a panel for adhesion test (aluminum plate, polyphthalamide (PPA) resin plate, and silver plate). The curable silicone composition was charged into the hole of the spacer and then left in a circulating hot air oven at 150° C. for 1 hour to produce a cylindrical cured product having a diameter of 5 mm and a height of 2 mm. This cured product was peeled off at a rate of 50 mm/min using a die shear strength measurement device to measure the load (MPa) at this time.

The curable silicone composition was used to produce a surface-mounted type light emitting diode (LED) as described below.

Production of Light Emitting Diode

In a cylindrical frame 5 that was made from polyphthalamide (PPA) resin and that had a closed bottom (inner diameter: 2.0 mm; depth: 1.0 mm), lead frames 2 and 3 were extended from side walls of the frame 5 toward the center of inner bottom of the frame 5. An LED chip 1 was mounted on the central part of the lead frame 2, and the LED chip 1 and the lead frame 3 were electrically connected by a bonding wire 4 in an unencapsulated light emitting diode. To the unencapsulated light emitting diode, the curable silicone composition that had been degassed was injected using a dispenser. Thereafter, the light emitting diode illustrated in FIG. 1 was produced by being heated in a heating oven at 100° C. for 30 minutes and then at 150° C. for 1 hour and curing the curable silicone composition.

Ink Test

Sixteen light emitting diodes produced by the method described above were immersed in a commercially available red ink and left at 50° C. for 24 hours. After the light emitting diodes were left, degrees of immersion of the red ink into the light emitting diodes were observed using a microscope and evaluated as follows.

⊚: Immersion of the ink was observed in two or less light emitting diodes.

Δ: Immersion of the ink was observed in three to eight light emitting diodes.

x: Immersion of the ink was observed in nine or more light emitting diodes.

Wire Breakage

Sixteen light emitting diodes produced by the method described above were subjected to 1,000 cycles of heat cycle test, in which 1 cycle thereof include a temperature cycle of −40° C. for 30 minutes and then 125° C. for 30 minutes. Thereafter, LEDs were lighted up by turning on the electricity and evaluated as follows.

⊚: Fourteen or more light emitting diodes were lighted up.

○: Eight to thirteen light emitting diodes were lighted up.

Δ: Seven or less light emitting diodes were lighted up.

TABLE 1

| Item | Category | Present invention | | | |
|---|---|---|---|---|---|
| | | Example 4 | Example 5 | Example 6 | Example 7 |
| Composition of curable silicone composition (part by mass) | Component (A-1) | 60 | 60 | 60 | — |
| | Component (A-2) | — | — | — | 53 |
| | Component (A-3) | 15 | 15 | 15 | 23 |
| | Component (B-1) | 17.9 | 17.9 | 17.9 | 16 |
| | Component (C-1) | 1.0 | — | — | 1.0 |
| | Component (C-2) | — | 1.0 | — | — |
| | Component (C-3) | — | — | 1.0 | — |
| | Component (C-4) | — | — | — | — |
| | Component (D-1) | 2.5 ppm | 2.5 ppm | 2.5 ppm | 5 ppm |
| | SiH/Vi | 1.0 | 1.0 | 1.0 | 0.88 |
| Adhesive strength (MPa) | | | | | |
| Aluminum plate | | 7 | 7 | 7 | 7 |
| PPA resin plate | | 8.3 | 8 | 7.5 | 7 |
| Silver plate | | 6.5 | 6.5 | 5 | 7 |
| Ink test | | ⊚ | ⊚ | ⊚ | ⊚ |
| Wire breakage | | ⊚ | ⊚ | ⊚ | ⊚ |

| Item | Category | Comparative Examples | | |
|---|---|---|---|---|
| | | Comparative Example 1 | Comparative Example 2 | Comparative Example 3 |
| Composition of curable silicone composition (part by mass) | Component (A-1) | 60 | 60 | — |
| | Component (A-2) | — | — | 53 |
| | Component (A-3) | 15 | 15 | 23 |
| | Component (B-1) | 17.9 | 17.9 | 16 |
| | Component (C-1) | — | — | — |
| | Component (C-2) | — | — | — |
| | Component (C-3) | — | — | — |
| | Component (C-4) | 1.0 | — | — |
| | Component (D-1) | 2.5 ppm | 2.5 ppm | 5 ppm |
| | SiH/Vi | 1.0 | 1.0 | 0.88 |
| Adhesive strength (MPa) | | | | |
| Aluminum plate | | 6 | 4 | 6 |
| PPA resin plate | | 5 | 5 | 5 |
| Silver plate | | 5 | 3 | 5 |
| Ink test | | Δ | X | Δ |
| Wire breakage | | Δ | ⊚ | Δ |

Examples 8 and 9 and Comparative Examples 4 and 5

The curable silicone compositions shown in Table 2 were prepared using the components described below. Note that, in Table 2, the content of component (D) is expressed in terms of the content (ppm; in terms of a mass unit) of platinum metal relative to the amount of the curable silicone composition. Furthermore, SiH/Vi in Table 2 shows the number of moles of silicon atom-bonded hydrogen atom in component (B) per 1 mol total of alkenyl groups contained in components (A) and (C).

The following components were used as component (A) in addition to component (A-2) described above. Furthermore, the viscosity was the value at 25° C. and was measured using a type B viscometer in accordance with JIS K 7117-1. Furthermore, the content of the vinyl group was measured by analysis using FT-IR, NMR, GPC, and the like.

Component (A-4): a dimethylpolysiloxane capped at both molecular terminals with dimethylvinylsiloxy groups (vinyl group content=0.48 mass %), having a viscosity of 300 mPa·s, and represented by the following average formula:

Me$_2$ViSiO(Me$_2$SiO)$_{150}$SiMe$_2$Vi

Component (A-5): a dimethylpolysiloxane capped at both molecular terminals with dimethylvinylsiloxy groups (vinyl group content=0.15 mass %), having a viscosity of 10,000 mPa·s, and represented by the following average formula:

Me$_2$ViSiO(Me$_2$SiO)$_{500}$SiMe$_2$Vi

Component (A-6): an organopolysiloxane resin having two or more vinyl groups in a molecule (vinyl group content=5.4 mass %), being a white solid at 25° C. and soluble in toluene, and represented by the following average unit formula:

(Me$_2$ViSiO$_{1/2}$)$_{0.15}$(Me$_3$SiO$_{1/2}$)$_{0.47}$(SiO$_{4/2}$)$_{0.38}$(HO$_{1/2}$)$_{0.0001}$

Component (A-7): an organopolysiloxane having two or more vinyl groups in a molecule (vinyl group content=4.2 mass %), being a white solid at 25° C. and soluble in toluene, and represented by the following average unit formula:

(Me$_2$ViSiO$_{1/2}$)$_{0.15}$(Me$_3$SiO$_{1/2}$)$_{0.38}$(SiO$_{4/2}$)$_{0.47}$(HO$_{1/2}$)$_{0.01}$

Component (A-8): an organopolysiloxane having two or more vinyl groups in a molecule (vinyl group content=5.6 mass %), being a white solid at 25° C. and soluble in toluene, and represented by the following average unit formula:

(PhSiO$_{3/2}$)$_{0.75}$(Me$_2$ViSiO$_{1/2}$)$_{0.25}$

The following components were used as component (B) in addition to component (B-1) described above.

Component (B-2): a polymethylhydrogensiloxane capped at both molecular terminals with trimethylsiloxy groups (silicon atom-bonded hydrogen atom content=1.6 mass %), having a viscosity of 20 mPa·s, and represented by the following average formula:

Me$_3$SiO(MeHSiO)$_{55}$SiMe$_3$

Component (B-3): a branched organopolysiloxane having two or more silicon atom-bonded hydrogen atoms in a molecule (silicon atom-bonded hydrogen atom content=0.65 mass %), having a viscosity of 25 mPa·s, and represented by the following average unit formula:

(PhSiO$_{3/2}$)$_{0.4}$(HMe$_2$SiO$_{1/2}$)$_{0.6}$

As component (C), components (C-1) and (C-4) described above were used.

The following components were used as component (D).

Component (D-2): a solution of a platinum-1,3-divinyltetramethyldisiloxane complex in 1,3-divinyltetramethyldisiloxane (platinum metal content=approximately 5,000 ppm)

The following component was used as component (E).

Component (E-1): 1-ethynylcyclohexan-1-ol

Hardness of the curable silicone composition was measured as follows.

Hardness of Cured Product

The curable silicone compositions were press-molded at 150° C. for 1 hour at a pressure of 5 MPa to produce sheet-like cured products. The hardness of the sheet-like cured product was measured by a type A durometer as specified in JIS K 6253. The results are shown in Table 2.

The curable silicone composition was used to produce a surface-mounted type light emitting diode (LED) as described below.

Production of Light Emitting Diode

In a cylindrical frame 5 that was made from polyphthalamide (PPA) resin and that had a closed bottom (inner diameter: 2.0 mm; depth: 1.0 mm), lead frames 2 and 3 were extended from side walls of the frame toward the center of inner bottom of the frame. An LED chip 1 was mounted on the central part of the lead frame 2, and the LED chip 1 and the lead frame 3 were electrically connected by a bonding wire 4 in an unencapsulated light emitting diode. To the unencapsulated light emitting diode, the curable silicone composition that had been degassed was injected using a dispenser. Thereafter, the surface-mounted type light emitting diode illustrated in FIG. 1 was produced by being heated in a heating oven at 100° C. for 30 minutes and then at 150° C. for 1 hour and curing the curable silicone composition.

Initial Peeling Proportion of Cured Product

For 20 light emitting diodes produced by the method described above, peeling conditions between the lead frames 2 and 3 and the bonding wire 4, and the cured product 6 were observed using an optical microscope. The proportion of the number of the light emitting diode in which peeling was observed is shown in Table 2.

Peeling Proportion after Moisture Absorption Reflow

For 20 light emitting diodes produced by the method as described above, peeling conditions between the lead frames 2 and 3 and the bonding wire 4, and the cured product 6 were observed using an optical microscope after the light emitting diodes were placed in a constant-temperature and constant-humidity chamber at 85° C. and 85% for 168 hours, then placed in an oven at 280° C. for 30 seconds, and placed at room temperature (25° C.). The proportion of the number of the light emitting diode in which peeling was observed is shown in Table 2.

TABLE 2

| Item | Category | Present invention | | Comparative Examples | |
|---|---|---|---|---|---|
| | | Example 8 | Example 9 | Comparative Example 4 | Comparative Example 5 |
| Composition of curable silicone composition (part by mass) | Component (A-3) | — | 50 | — | 50 |
| | Component (A-4) | 40 | — | 40 | — |
| | Component (A-5) | 20 | — | 20 | — |
| | Component (A-6) | 15 | — | 15 | — |
| | Component (A-7) | 20 | — | 20 | — |
| | Component (A-8) | — | 35 | — | 35 |
| | Component (B-1) | — | 10 | — | 10 |
| | Component (B-2) | 5.5 | — | 5.5 | — |
| | Component (B-3) | — | 5 | — | 5 |
| | Component (C-1) | 0.5 | 0.5 | — | — |
| | Component (C-4) | — | — | 0.5 | 0.5 |
| | Component (D-2) | 5 | 5 | 5 | 5 |
| | Component (E-1) | 0.1 | 0.1 | 0.1 | 0.1 |
| | SiH/Vi | 1.27 | 0.96 | 1.27 | 0.96 |

TABLE 2-continued

| Item | Category | Present invention | | Comparative Examples | |
|---|---|---|---|---|---|
| | | Example 8 | Example 9 | Comparative Example 4 | Comparative Example 5 |
| | Type A hardness of cured product | 70 | 50 | 70 | 50 |
| | Peeling rate | | | | |
| | Initial | 0/20 | 0/20 | 0/20 | 0/20 |
| | After moisture absorption reflow | 0/20 | 0/20 | 20/20 | 20/20 |

From the results shown in Table 2, it was clear that cured products of the curable silicone compositions of Examples 8 and 9 exhibited higher peeling resistance compared to those of curable silicone compositions of Comparative Examples 4 and 5.

INDUSTRIAL APPLICABILITY

The curable silicone composition of the present invention is a composition that has excellent flowability and which is cured to form a cured product in which phosphors are homogeneously dispersed and that has a high refractive index, and is therefore suitable for use as a sealing agent or coating agent for light emitting elements in optical semiconductor devices such as light emitting diodes (LEDs).

DESCRIPTION OF SYMBOLS

1 Light emitting element
2 Lead frame
3 Lead frame
4 Bonding wire
5 Frame
6 Cured product of curable silicone composition

The invention claimed is:
1. An organosiloxane represented by the general formula:

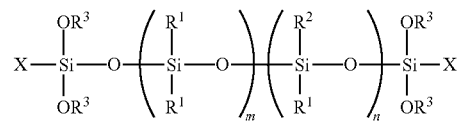

wherein, $R^1$ are the same or different monovalent hydrocarbon groups each having from 1 to 12 carbons but having no aliphatic unsaturated bond, $R^2$ is an alkenyl group having from 2 to 12 carbons, $R^3$ are the same or different alkyl groups each having from 1 to 3 carbons, X is a group represented by the general formula:

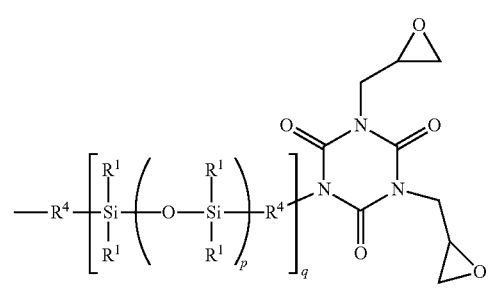

wherein, $R^1$ are the same as those described above, $R^4$ are the same or different alkylene groups, p is an integer of 0 to 50, and q is 0 or 1, wherein, m is an integer of 0 to 50, and n is an integer of 1 to 50.

2. The organosiloxane according to claim 1, wherein $R^4$ is an ethylene group or a propylene group.

3. An adhesion promoter comprising the organosiloxane according to claim 1.

4. A curable silicone composition comprising the organosiloxane according to claim 1 as an adhesion promoter.

5. The curable silicone composition according to claim 4, wherein the curable silicone composition is cured by a hydrosilylation reaction.

6. The curable silicone composition according to claim 5, the hydrosilylation reaction curable silicone composition comprising:
   (A) 100 parts by mass of an organopolysiloxane having at least two alkenyl groups in a molecule;
   (B) an organohydrogenpolysiloxane having at least two silicon atom-bonded hydrogen atoms in a molecule, in an amount such that provides from 0.1 to 10 mol of silicon atom-bonded hydrogen atom per 1 mol total of alkenyl groups contained in components (A) and (C);
   (C) from 0.1 to 10 parts by mass of an adhesion promoter containing the organosiloxane; and
   (D) a catalyst for hydrosilylation reaction, in an amount that is sufficient to promote curing of the composition.

7. The curable silicone composition according to claim 6, further comprising (E) a hydrosilylation reaction inhibitor, in an amount from 0.0001 to 5 parts by mass of per 100 parts by mass total of components (A) to (D).

8. A semiconductor device comprising a semiconductor element encapsulated with a cured product of the curable silicone composition according to claim 4.

9. The semiconductor device according to claim 8, wherein the semiconductor element is a light emitting element.

10. An adhesion promoter comprising the organosiloxane according to claim 2.

* * * * *